United States Patent [19]

Leonidov et al.

[11] Patent Number: 5,510,387
[45] Date of Patent: Apr. 23, 1996

[54] ANTIMICROBIAL INTERFERON-INDUCING MEDICAMENT

[75] Inventors: Nikolai B. Leonidov, Moscow; Nikolai G. Seleznev, Ryazan, both of Russian Federation

[73] Assignee: Nikolai Borisovich Leonidov, Moscow, Russian Federation

[21] Appl. No.: 256,494

[22] PCT Filed: Aug. 31, 1993

[86] PCT No.: PCT/RU93/00209

§ 371 Date: Jul. 13, 1994

§ 102(e) Date: Jul. 13, 1994

[87] PCT Pub. No.: WO94/10977

PCT Pub. Date: May 26, 1994

[30] Foreign Application Priority Data

Nov. 16, 1992 [RU] Russian Federation ............. 92006718
Jan. 20, 1993 [RU] Russian Federation ............. 93004015

[51] Int. Cl.⁶ .......................... A61K 31/18; A61K 38/21; A61K 31/505
[52] U.S. Cl. .............................................................. 514/603
[58] Field of Search .............................................. 514/603

[56] References Cited

U.S. PATENT DOCUMENTS 4,401,663 8/1983 Buckwalter et al. ................. 424/321
5,151,265 9/1992 Hwang-Felgner et al. ............ 424/85.5

FOREIGN PATENT DOCUMENTS 2321283 3/1977 France .
2361103 3/1978 France .
3800256 7/1988 Germany .

OTHER PUBLICATIONS

Melent'Eva, G. "Pharmaceutic Chemistry" Moscow, 1968, pp. 285–286.
Mashkovsky, M., "Medical Substances" *Handbook on Pharmacotherapy for Medical Practitioners*, 1984, pp. 275–277.
Mashkovsky, M., "Medicinal Substances" *Handbook on Pharmacotherapy for Medical Practitioners*, 1986, pp. 169–171.
Zhdanoy, V., Ed., "Interferon Inducers" *USSR Academy of Science*, 1982, pp. 7 to 18.
Lin, H., et al., "Polymorphism in Sulfanilamide–dy" Journal of Pharmaceutical Studies vol. 59, No. 7, Jul. 1970, pp. 972 to 975.
Watanabe, A., "The Phenomenon of Polymorphism in Sulfanilamide", 1985.

Primary Examiner—Marianne Cintins
Assistant Examiner—Keith MacMillan
Attorney, Agent, or Firm—Ladas & Parry

[57] ABSTRACT

An antimicrobial and interferon-inducing composition containing the crystalline gamma-modification of para-amino benzenesulfanilamide and a method for inducing interferon by administering a composition containing crystalline gamma-modification of para-amino benzenesulfanilamide.

7 Claims, No Drawings

ANTIMICROBIAL INTERFERON-INDUCING MEDICAMENT

This application is a 371 of PCT/Ru93/00209 filed Aug. 31, 1993.

FIELD OF ART

The present invention relates to medicine and, more specifically, to an antimicrobial and interferon-inducing medicament.

BACKGROUND OF ART

Widely known in the prior art is administration of para-aminobenzenesulfamide (Streptocidum album, Sulfanilamidum), one of the chemotherapeutic preparations of sulfanilamide group. The preparation exerts an antimicrobial effect with relation to streptococcus, meningococcus, gonococcus, pneumococcus, colibacillus and some other bacteria. Said preparation is utilized predominantly in a tablet form. Injection forms of said preparation presuppose their conversion into soluble salts, for example, the formation of soluble compounds through a primary aromatic group. However, this structure is unstable and calls for introducing a stabilizer, i.e. toxic sodium sulfite (M. D. Mashkovsky "Medicinal Drugs", Moscow, "Meditsina", 1984, vol. 2, p. 275–277; G. A. Melentieva, "Pharmaceutical Chemistry", Moscow, "Meditsina", 1986, p. 285–286). In addition, the antimicrobial effect of said preparation is exhibited only in presence of an open aminogroup in a para-position to the sulfanilamide group, so that the degree of its opening and, consequently, its antimicrobial effect well depend on time and on physiological constants of blood. This currently-used preparation in a soluble form (Streptocidum Solubile) features a number of negative properties, such as side effects associated with administration of a toxic stabilizer, irritant effect, low biological availability.

It is common knowledge that para-aminobenzenesulfanilamide can crystallize in the form of three polymorphic modifications designated by α-, β-, γ-forms (Journal of Pharmaceutical Sciences, v. 58, 59, No. 7, July 1970, p. 972–975; Journal of Pharmaceutical Sciences of Japan, 1942, m.63, No.11, p. 17–19) of which only α-form is used in practical medicine. The pharmacokinetic properties of the crystalline γ-modification of para-aminobenzenesulfanilamide have not been described. The use of γ-modification as an active principle of the medicament is unknown. Besides, the use of α-, β- and γ-modifications of para-aminobenzenesulfanilamide in the capacity of interferon inducers is not known either.

It is common knowledge that all inducers of interferon, the most important factor of nonspecific resistance of cells, are divided into two groups, viz., natural (viruses and natural two-spiral nucleic acids) and synthetic (polymers and low-molecular preparations) (F. I. Ershov et al, collected works "Interferon Inducers", Moscow, 1982, p. 7–18).

The natural inducers of interferon are highly antigenic, can be contaminated by other dangerous microorganisms and all of them exert a toxic effect in concentrations requisite for displaying sufficient antiviral activity. The same disadvantages are inherent in the majority of high-molecular synthetic interferon inducers—polycarboxylates and polynucleotides (type poly (И) and poly (Ц). They are likewise sufficiently toxic while their synthesis is difficult and economically unremunerative.

Clinically promising are also such low-molecular interferon inducers as gossypol analogs, thyloron preparation (2,7-bis-(2-diethylaminoethoxy)-3-fluorenon) and levamisol (−) 2,3,5,6-tetrahydro-6-phenyl-imidaso-(2,1-B)-thiazole hydrochloride) (M. D. Mashkovsky, "Medicinal Drugs", Moscow, "Meditsina", 1986, vol. 2 p. 169–171).

However, all these preparations are noted for high toxicity and numerous side effects, and, what is more, interferon induction shows up after administration of large doses and is effective for a short time only.

DISCLOSURE OF THE INVENTION

The main object of the invention resides in developing a new medicinal drug possessing an antimicrobial and interferon-inducing effect, a high therapeutic efficiency, low toxicity, absence of side effects, and in reducing the time of treatment at diminished doses.

This object of attained by providing a medicinal preparation with an antimicrobial and interferon-inducing effect containing an active principle and a pharmaceutic diluent wherein, according to the invention, the active principle is constituted by a crystalline γ-modification of para-aminobenzenesulfanilamide. The claimed medicament can be administered in any pharmaceutically-acceptable form. When used for injections it preferably contains 1.0–2.5 wt.-% of active principle.

The claimed medicament used for injections may contain additionally a low-molecular polyvinylpyrrolidone in the following ratio of components, wt.-%:

| | |
|---|---|
| Crystalline γ-modification of para-aminobenzenesulfanilamide | 1.5–2.5 |
| Low-molecular polyvinylpyrrolidone | 2.0–4.0 |
| Pharmaceutical diluent | the balance |

The pharmaceutic diluent in the claimed preparation for injections shall preferably be water for injections.

The claimed medicament may be administered in the form of rectal suppositories, preferably containing 12.5–17.5 wt.-% of active principle. The pharmaceutic diluent (base) of rectal suppositories may be any suitable fat, cocoa butter, etc.

The claimed medicament may be prescribed for external use, preferably in combination with 2,4-dioxo-6-methyl-1, 2,3,4-tetrahydropirimidine in a 50:50 proportion by weight.

The claimed medicament containing, according to the invention, a crystalline γ-modification of para-aminobenzenesulfanilamide for the active principle, features a high antimicrobial activity which is as good as that of officially used pharmacopeial para-aminobenzenesulfanilamide (α-modification), a lower toxicity, improved biological availability and negligible side effects. Due to the improved biological availability of the claimed medicament, which is 2.43 times that of the known pharmacopeical preparation, its therapeutic dose and time of treatment can be reduced and side effects eliminated. Besides, the claimed medicament exhibits a high interferon-inducing activity (the pharmacopeial para-aminobenzenesulfanilamide lacks such activity). A combination of high interferon-inducing activity with antimicrobial activity at a low toxicity and availability renders the claimed medicament quite promising for a wide range of applications in practical treatment of infections.

BEST MODE OF CARRYING OUT THE INVENTION

The claimed antimicrobial and interferon-inducing medicament according to the invention has an active principle in the form of a crystalline γ-modification of para-aminobenzenesulfanilamide. The toxic properties of the claimed medicament have been thoroughly investigated experimentally "in vitro" and "in vivo". Acute toxicity of the solutions of the pharmacopeial and claimed preparations for injections has been investigated on male rats weighing 150–200 g, 2 ml of known preparation was administered intraperitoneally to each animal in the first group while each animal of the second group received 2 ml of the claimed medicament containing, wt.-%: γ-modification of para-aminobenzenesulfanilamide, 2.0; low-molecular polyvinylpyrrolidone, 3.0; water for injections, the balance; the third group of animals received 2 ml of water for injections. The animals were observed for 10 days after which the median lethal dose $LD_{50}$ was calculated. Experiments have shown that $LD_{50}$ of the claimed medicament is 1918 mg/kg of animal body weight while in the pharmacopeial preparation it is 1245 mg/kg of body weight.

An analysis of the data gained has revealed a lower toxicity (by 54.4%) of the claimed medicament as compared with the known one.

Toxic effects of the claimed medicament in comparison with those of the known one have been studied on the basis of a pathomorphological examination of animals' organs followed by a histological assessment.

Microscopic structure of organs has been studied by killing the test and control animals after certain periods of time. Pieces of organs were fixed with a 10–12-% solution of neutral formalin, poured over with paraffin, and sections 8–10 mm thick with colored with hematoxin-eosin.

A histological examination has been conducted on femoral muscles, heart, lungs, liver, kidney, spleen. The histological examination of the injection form of the known preparation has revealed hemorrhages of various depth (for small to extensive ones) in the zone of intramuscular injection in the femoral muscles. The muscular tissue in the hemorrhage zone exhibited disturbances in the general structure of muscular fibers (for vanished transverse striction to necrosis.

Intramuscular injection of the claimed medicament for injections produced no pathological changes in the muscles.

Thus, the claimed medicament has no irritating effect inherent in the known preparation.

Histological examinations of the other organs have shown absence of substantial changes caused by administration of the claimed medicament as compared with the known one.

Thus, experiments on animals have demonstrated absence of side effects caused by administration of the claimed medicament.

The specific antimicrobial activity of the claimed medicament was studied by a method of serial dilutions. The source solutions were a 0.5-% solution of pharmacopeial para-aminobenzenesulfanilamide and γ- modification of para-aminobenzenesulfanilamide—active principle—of the claimed medicament in a 0.01 n solution of sodium hydroxide. Doubled dilutions of the test solutions were prepared in beef-extract broth with a culture of Staphylococcus aureus added. The inoculum was held for 24 h in a thermostat and the bacteriostatic concentration was assessed visually.

The tests were carried out with sterile and nonsterile solutions of pharmacopeial preparation and active principle of the claimed medicament.

The experiments were conducted three times on three series of test solutions.

The results of the tests are shown in Table 1.

TABLE 1

Comparative Characteristic of Growth of *Staphylococcus Aureus* Culture Acted upon by Para-Aminobenzenesulfanilamide and by Crystalline γ-modification - Active Principle - of Claimed Medicament

| No. | Test medicament | 0 | 1 | 2 | 3 | Control |
|---|---|---|---|---|---|---|
| 1. | Sterile solvent | none | yes | yes | yes | yes |
| 2. | Pharmacopeial para-aminobenzene-sulfanilamide | none | none | none | yes | yes |
| 3. | γ-modification of para-aminobenzene-sulfanilamide | none | none | none | yes | yes |
| 4. | Nonsterile solvent | none | yes | yes | yes | yes |
| 5. | Pharmacopeial para-aminobenzenesulfa-nilamide (nonsterile medicament) | none | none | none | yes | yes |
| 6. | γ-modification of para-aminobenzene-sulfanilamide (non-sterile medicament) | none | none | none | yes | yes |

(Duration (days), Growth (visually))

An analysis of the data in Table 1 gives an evidence that the active principle of the claimed medicament features an antimicrobial activity which is as good as that of the pharmacopeial (official) preparation.

The interferon-inducing activity of the claimed medicament as compared with the pharmacopeial preparation was tested on mice in vivo.

Experiments were conducted on male mice, line CBA, weighing 10–12 g. The cell culture was constituted by an inoculated line of cells of mouse fibroblasts Z-929. The cells were grown in plastic 96-hole plate (37 C, 3.5% CO) in Eagle medium 2 MEM, of 10-% cattle serum. The selected virus was the virus of encephalocarditis of mice, strain Columbia.

The pharmacopeial preparation and the claimed medicament were administered once intraperitoneally to not less than 5 animals in does of 50, 150 mkg/0.2 ml (0.2 ml per mouse). Blood was drawn from the carotid artery 5, 24 and 72 h after administration of preparations. Interferon was titrated by determining the suppression of the cytopathic effect on the cell culture by a micromethod. The results of tests are summarized in Table 2.

TABLE 2

Dynamics of Interferon Formation in Blood Serum of Mice after Injection of Test Preparations

| | | Time of blood draw after administration of preparation, h | Interferon titers, un/ml | |
|---|---|---|---|---|
| No. | Preparation | | concentration of preparation, 50 mkg/mouse | concentration of preparation, 150 mkg/mouse |
| 1. | Pharmacopeial para-aminobenzenesulfanilamide | 5 | <20 | <20 |
| | | 24 | <20 | <20 |
| | | 72 | <20 | <20 |
| 2. | Claimed medicament | 5 | 40–80 | 80 |
| | | 24 | 160 | 320 |
| | | 72 | <20 | <20 |
| 3. | Control | 5 | <20 | |
| | | 24 | <20 | |

TABLE 2-continued

Dynamics of Interferon Formation in Blood Serum of Mice after Injection of Test Preparations

| No. | Preparation | Time of blood draw after administration of preparation, h | Interferon titers, un/ml concentration of preparation, 50 mkg/mouse | concentration of preparation, 150 mkg/mouse |
|---|---|---|---|---|
| 4. | Mouse serum interferon | 72 — | | <20 640 |

An analysis of test results has demonstrated that the pharmacopeial preparation has no interferon-inducing activity. At the same time the claimed medicament has induced interferon in blood serum of mice already 5 h after its administering (early interferon) with its activity of 40–80 un/ml while after 24 h the interferon titers have reached 160–320 un/ml. After 72 h the interferon titers diminished.

A comparison of the test results with the data known from literature gives ground to a conclusion that γ-modification is a highly-active inducer of interferon.

A comparative characteristic of activity of the known interferon inducers and that of the claimed medicament is presented in Table 3.

TABLE 3

Comparative Characteristic of Interferon Inducers

| Interferon inducer | Activity, un/ml |
|---|---|
| Active inducer | 30–100 |
| High-active inducer | >100 |
| Poly (И) Poly (Ц) | >1000 |
| Dextransulfate | 60–80 |
| Levamisol | >100 |
| Gossypol | 80 |
| Trental | 80–160 |
| Euphylline | 80 |
| γ-modification of para-aminobenzenesulfanilamide (active principle of claimed medicament) | 160–320 |

The data of Table 3 lead to a conclusion that the claimed medicament is a high-active inducer (activity 160–320 un/ml).

For studying the biological availability of the claimed medicament in comparison with the known preparation (Streptocidum solubile) we have investigated the following factors: 1) maximum concentration of the drug in blood; 2) time of reaching a maximum concentration; 3) time changes in the concentration of substance in blood plasma or serum.

Tests were made on rabbits, body weight 3 kg. The doses of preparation were calculated on the basis of therapeutic doses and were 100 mg/kg. The difference of molecular masses of substances (equimolar relation) was taken in account. Blood was collected 0.5, 1, 2, 4, and 6 hours after a single-shot intramuscular injection of the preparation and the same was analyzed by the Prebsting-Gavrilova method.

The data obtained are summarized in Table 4.

TABLE 4

Content of Preparation in Blood after Intramuscular Injection

| Medicament for injections | Concentration of sulfamilamide in blood, mkg/ml, hours after injection | | | | |
|---|---|---|---|---|---|
| | 0.5 | 1 | 2 | 4 | 6 |
| Known preparation (Streptocidum solubile) | 2.5 +. 6.8 | 9.81 + 3.9 | 6.99 + 1.4 | 5.08 + 0.74 | 2.94 + 0.78 |
| Claimed medicament, wt.-%: γ-modification of para-aminobenzenesulfanilamide, 2.0; polyvinylpyrrolidone, 3.0; water for injections, the balance | 12.61 + 3.1 | 13.46 + 4.4 | 14.59 + 3.45 | 9.04 + 0.81 | 7.84 + 0.86 |

The data obtained are an evidence that the biological availability of the claimed medicament is 2.43 times that of the known preparation. This enables the curative dose of the preparation to be correspondingly reduced 2.43 times which will contribute to a still stronger smoothing out of its side effects. At the same time, owing to a high biological availability, a therapeutic dose of the claimed medicament can intensify the bacteriostatic action of the drug, thereby promoting its therapeutic effect.

The claimed medicament is utilized in the capacity of an antimicrobial and interferon-inducing drug.

The claimed medicament can be administered in any pharmaceutically-suitable medicamentous form. When it is used for injections, the content of active principle ranges from 1.5 to 2.5 wt.-%. Investigations in selecting the optimum concentration of the active principle have demonstrated that the claimed concentration range ensures the requisite therapeutic concentration of preparation in blood. The content of active principle in blood below 1.5 wt.-% builds up concentration which is close to the lower limits of the therapeutic concentration. Conversely, concentration exceeding 2.5 wt.-% increases load on the muscular tissue which upsets the general structure of muscular fibers. And still higher doses bring about a risk of toxic concentrations in blood.

The claimed preparation for injections may additionally contain low-molecular polyvinylpyrrolidone in the following proportions of components, wt.-%:

| | |
|---|---|
| crystalline γ-modification of para-aminobenzenesulfanilamide | 1.5–2.5 |
| low-molecular polyvinylpyrrolidone | 2.0–4.0 |
| pharmaceutic diluent | the balance |

Introduction of polyvinylpyrrolidone into the preparation is warranted by its indifference and requisite sedimentation stability and absorbability of the composition. The time of sedimentation is established experimentally.

A higher concentration of polyvinylpyrrolidone increases sedimentation stability. An analysis of concentration of the preparation in blood has shown that the optimum limits of polyvinylpyrrolidone content in the preparation is 2–4 wt.-%. The pharmaceutic diluent is, preferably, water for injections.

The claimed preparation can be used in the form of rectal suppositories containing, preferably, 12.5–17.5 wt.-% of active principle. An analysis of conducted investigations has shown that administration of suppositories containing 12.5–17.5 wt.-% of the active principle ensures its therapeutic concentration in blood (2.0–20.0 mkg/ml). The suppositories may be made on any pharmaceutically-suitable base (fat, cocoa butter, etc.). The claimed preparation can be used for external application in which case its active principle is the crystalline γ-modification of para-aminobenzenesulfanilamide in combination with 2,4-dioxo-6-methyl-1,2,3,4-tetrahydropyrimidine in a mass proportion of 1:1.

The claimed preparation in the form of ointment or powder for external application has been tested clinically in severest cases of poorly-healing purulent wounds of various nosological forms (trophic ulcers of venous origin: small, up to 5 sq.cm, and large, over 5 sq.cm in size, and postoperative purulent wounds).

The program of tests was accentuated on weakening of the inflammatory reaction, time of wound cleaning, granulation growth rate, marginal epithelization. For the sake of comparison, the patients were treated with the known ointment containing 10 wt.-% of active principle, i.e. 4-dioxo-6-methyl-1,2,3,4-tetrahydropyrimidine.

The use of the claimed preparation for treatment of trophic ulcers of venous origin brought about an essential weakening of the inflammatory reaction in the first two days, stimulated the rate of granulation growth and ensured prompt epithelization. Ulcers up to 2 cm in diameter were healed within 7–10 days (as compared with conventional treatment time of 14–18 days). The postoperative purulent wounds 4 to 20 sq.cm in size were quickly cleaned, rubber and inflammatory infiltration on wound edges diminished and vanished, pains subsided on the 2nd or 3rd day, granulations turned bright and fine-grained. The healing time was reduced twice.

The results of investigations appear in Tables 5 and 6.

TABLE 5

Average Time (days) for Healing Wounds with Claimed and Known Medicaments

| | Healing time (days) | |
|---|---|---|
| Nosological form of wounds | claimed medicament | known ointment |
| Trophic ulcer of venous origin, up to 5 sq.cm in size | 9 | 16 |
| Trophic ulcer of venous origin, over 5 sq.cm in size | 18 | 35 |
| Purulent postoperative wounds | 8 | 15 |

TABLE 6

Results of Healing Wounds with Claimed Medicament in Comparison with Known Ointment

| | | Treatment results | | | |
|---|---|---|---|---|---|
| | | claimed medicament | | known ointment | |
| Nosological form of wounds | Number of patients | improvement | no progress | improvement | no progress |
| Trophic ulcers of venous origin | 12 | 6 | — | 3 | 3 |
| Purulent postoperative wounds | 12 | 6 | — | 4 | 2 |

Now the invention will be elucidated by concrete examples of preparing and testing the claimed medicament.

EXAMPLE 1

The medicament was prepared in aseptic conditions.

2 g of low-molecular polyvinylpyrrolidone (molecular mass 12000) was dissolved in a small amount of water (or injections, the produced solution was treated with 1.5 g of powder of γ-modification of para-aminobenzenesulfanilamide, particle size under 0.1 micron, shaken for 15–20 s, the volume of produced suspension was brought to 100 ml was distilled water for injections, and shaken once more.

The produced medicament for injections is a suspension with an optical density of 2.3. After 5 minutes' settling the optical density was 2.2, pH=6.5.

Five 3-kg rabbits were given intramuscularly, each, 3 ml of prepared suspension.

After 0.5, 1, 2, 4, 6 hours 1 ml of blood was drawn from the auricular vein of rabbits and analyzed by the known method (Prebsting-Gavrilova).

The obtained experimental data were statistically processed (p=95%). Experimental data are summarized in Table 7.

TABLE 7

Content of Claimed Medicament in Blood after Intramuscular Injection
Content of medicament in blood (mkg/ml)

| 0.5 h | 1 h | 2 h | 4 h | 6 h |
|---|---|---|---|---|
| 44.43 + 0.70 | 5.0 + 0.88 | 5.82 + 0.62 | 3.30 + 0.5 | 3.04 + 0.48 |

It can be seen from Table 7 that the therapeutic concentration of the medicament in blood is retained in the course of 6 h.

Histological control discovered no changes in internal organs.

EXAMPLE 2

The medicament was prepared in aseptic conditions.

4 g of low-molecular polyvinylpyrrolidone (molecular mass 12000) was dissolved in a small amount of water for injections and the produced solution was treated with 2.5 g of powder of γ-modification of para-aminobenzenesulfanilamide, particle size 0.1 micron and smaller, shaken for 15–20 s, the volume of the produced suspension was brought to 100 ml with distilled water for injections, and shaken once more.

The medicament for injections produced in this way had the form of a suspension with an optical density of 3.2. After 5-minutes' settling the optical density was 3.0 and pH=6.8.

Five 3-kg rabbits were injected intramuscularly, each, with 3 ml of prepared suspension.

After 0.5, 1, 2, 4 and 6 hours, 1 ml of blood was drawn from the auricular vein of rabbits and analyzed by the known method (Prebsting-Gavrilova).

The obtained experimental data were statistically processed (p=95%). They are given in Table 8, below.

TABLE 8

Concentration of Claimed Medicament in Blood after Intramuscular Injection
Concentration of claimed medicament in blood (mkg/ml)

| 0.5 h | 1 h | 2 h | 4 h | 6 h |
|---|---|---|---|---|
| 9.9 + 0.75 | 10.62 + 1.90 | 11.15 + 2.1 | 7.62 + 1.3 | 6.11 + 1.20 |

It can be derived from the Table that the therapeutic concentration of the claimed medicament in blood is retained for 6 h.

A histological examination discovered no changes in internal organs.

EXAMPLE 3

Interferon-inducing activity of the claimed medicament was tested as follows.

Tests were made on 10 male mice, line SVA, weighing 10–12 g each. The test culture was the inoculated line of cells of mouse fibroblasts Z-929. The cells were grown in 96-hole plastic plates (37 C, 3.5% CO) in Eagle medium MEM of 10-% cattle serum. The virus was of mouse encephalocarditis, strain Columbia.

Five mice were injected with the claimed medicament in a dose of 50 mkg/0.2 ml (1st group) and five mice received each, 150 mkg/0.1 ml intraperitoneally (2nd group). Blood was drawn from the carotid 5, 24 and 72 h administration of the preparation, interferon was titered by determining suppression of cytopathic action on the cell culture by the micromethod.

Already after 5 h the interferon level in blood serum of the 1st group of mice has reached 40–80 un/ml; after 24 h it increased to 160 un/ml and on expiration of 72 h, dropped to 20 un/ml.

In the 2nd group of animals 5 h after administration of the medicament the interferon level was 80 un/ml; it rose to 320 un/ml after 24 h while after 72 h it dropped to 20 un/ml.

Thus, administration of the claimed medicament in a dose of 50 and 150 un/ml produced a considerable increase of interferon titers: up to 40–80 un/ml after 5 h and up to 160–320 un/ml after 24 h.

An analysis of test results proves that the claimed medicament features a high interferon-inducing activity (160–320 un/ml).

EXAMPLE 4

Preparation and tests of the claimed medicament for rectal administration.

Suppositories are prepared by pouring-out method. Each suppository contains 0.3 g of active principle and 1.7 g of pharmaceutically-suitable fat base.

The γ-modification of para-aminobenzenesulfanilamide (active principle) is introduced into the melted base in the form of finely-divided powder at a temperature of 40°–45° C. The prepared suppositories are stored for two weeks at room temperature. Experiments are carried out on rabbits weighing 3–3.5 kg. Before introduction of suppositories, the rabbits are given a cleansing enema and after introduction the anal orifice is fixed with a clip.

Blood is drawn from the auricular vein after 0.5, 1, 2, 4 and 6 h. Concentration of medicament in blood is determined by the Prebsting-Gavrilova method. Concurrently, comparative tests are carried out with the pharmacopeial preparation of para-aminobenzenesulfanilamide.

TABLE 9

Concentration of Test Rectal Preparations in Blood (introduction of suppositories)

| No. | Preparation | Concentration, mkg/ml | | | | |
|---|---|---|---|---|---|---|
| | | 0.5 h | 1 h | 2 h | 4 h | 6 h |
| 1. | Pharmacopeial preparation | 5.13 + 1.3 | 5.83 + 1.4 | 13.32 + 2.15 | 13.72 + 1.29 | 8.20 + 1.41 |
| 2. | Claimed medicament | 17.32 + 1.40 | 10.97 + 0.95 | 6.41 + 0.96 | 5.48 + 1.12 | 3.83 + 1.13 |

An analysis of experimental data submitted in Table 9 illustrates that rectal suppositories containing the claimed medicament are more biologically available than those with the pharmacopeial preparation, they ensure maximum concentration already 0.5–1 h after administration and maintain the therapeutic concentration (within 2–20 mkg/ml) in the course of 6 h.

Tests have shown that the animals do not suffer from dyspeptic disorders. After post mortem dissection there were no changes of the mucous membrane in the large intestine.

Neither was there any distension of intestines. Filling of mesentery vessels with blood was normal. On dissection of the rectum the mucous membrane was pallid and macroscopic examination revealed no hemorrhage foci, necroses and other injuries.

Examination of histological sections fixed in 10% formalin and colored with hematoxyline and eosine has shown no substantial deviations from normal morphological structure.

An examination of the antimicrobial activity of the claimed suppositories has confirmed the presence of bacteriostatic effect on Gr+ and Gr− microbes.

Thus, the examinations have revealed that the claimed medicament for rectal use exhibits antimicrobial activity, high biological availability and no irritating side effects.

EXAMPLE 5

Clinical tests of the claimed medicament for external use.

Patient Z., 52, was admitted to hospital with a diagnosis of chronic venous insufficiency of the left lower extremity and trophic ulcer of the epigastric region 2×3 cm in size. After a Cokket operation the patient was given traditional medicaments such as dioxidine, vinyline and seabuckthorn oil. The ulcer was healing slowly. Healing was completed in 2 months.

Then a sinistral Cokket operation was made. In the course of the postoperative period the ulcer was treated daily with the claimed medicament (containing γ-modification of para-aminobenzenesulfanilamide in a mass relation of 1:1) followed by bandaging. Beginning from the second day the inflammatory reaction diminished, the wound cleared, granulations and marginal epithelization started growing intensively. Complete healing cam by the 18th day.

Patient K., 56, was admitted to hospital in connection with obliterating atherosclerosis, Leriche' syndrome. In the postoperative period after aorto-femoral-bifurcation shunting the operation wound was supported on the sinistrous side. The sutures were removed and the wound drained. On the second day after vanishing of purulent masses the wound was coated daily with the claimed medicament (containing γ-modification of para-aminobenzenesulfanilamide in combination with 2,4-dioxo-6-methyl-1,2,3,4-tetrahydropyrimidine in a mass relation of 1:1) followed by bandaging. Granulation came quickly and epithelization of the wound was completed in 9 days.

INDUSTRIAL APPLICABILITY

The claimed medicament features antimicrobial and interferon-inducing activity and is utilized in medical practice.

We claim:

1. A method of inducing interferon comprising administering to a patient a composition comprising an effective amount of crystalline gamma-modification of para-aminobenzenesulfanilamide in a pharmaceutically acceptable diluent or carrier.

2. A method according to claim 1 wherein the crystalline gamma-modification of para-aminobenzene sulfanilamide is present in the composition in an amount of from 1.5 to 2.5 weight % and said composition is administered to the patient by injection.

3. A method according to claim 2 wherein the composition further comprises low molecular weight polyvinylpyrrolidone.

4. A method according to claim 3 wherein the low molecular weight polyvinylpyrrolidone is present in an amount of from 2.0 to 4.0 weight %.

5. A method according to claim 1 wherein the crystalline gamma-modification of para-aminobenzenesulfanilamide is administered in a rectal suppository.

6. A method according to claim 5 wherein the crystalline gamma-modification of para-aminobenzenesulfanilamide in the suppository is present in an amount of from 12.5 to 17.5 weight %.

7. A method for inducing interferon according to claim 1 comprising applying topically a composition comprising the crystalline gamma-modification of para-aminobenzene sulfanilamide and 2,4-dioxo-6-methyl-1,2,3,4-tetrahydropyrimidine.

* * * * *

UNITED STATES PATENT AND TRADEMARK OFFICE
CERTIFICATE OF CORRECTION

PATENT NO. : 5,510,387
DATED : APRIL 23, 1996
INVENTOR(S) : Nikolai B. LEONIDOV and Nikolai G. SELEZNEV It is certified that error appears in the above-indentified patent and that said Letters Patent is hereby corrected as shown below:

Title page, item [57],
Abstract, line 2, delete "para-amino" and substitute therefor --para-aminobenzenesulfonamide--.

Title page, item [57],
Abstract, line 3, delete "benzenesulfanilamide".

Title page, item [57],
Abstract, line 5, delete "para-amino benzenesulfanilamide" and substitute therefor --para-aminobenzenesulfonamide--.

Column 1, line 39, delete "para-aminobenzenesulfanil-" and substitute therefor --para-aminobenzenesulfonamide--.

Column 1, line 40, delete "amide".

Column 1, line 46, delete "para-aminobenzenesulfanil-" and substitute therefor --para-aminobenzenesulfonamide--.

Column 1, line 47, delete "amide".

UNITED STATES PATENT AND TRADEMARK OFFICE
CERTIFICATE OF CORRECTION

PATENT NO. : 5,510,387
DATED : APRIL 23, 1996
INVENTOR(S) : Nikolai B. LEONIDOV and Nikolai G. SELEZNEV It is certified that error appears in the above-indentified patent and that said Letters Patent is hereby corrected as shown below:

Column 1, line 49, delete "para-aminobenze-" and substitute therefor --para-aminobenzenesulfonamide--.

Column 1, line 50, delete "nesulfanilamide".

Column 2, line 21, delete "para-ami-".

Column 2, line 22, delete "nobenzenesulfanilamide" and substitute therefor --para-aminobenzenesulfonamide--.

Column 2, line 31, delete "para-".

Column 2, line 32, delete "aminobenzenesulfanilamide" and substitute therefor --para-aminobenzenesulfonamide--.

Column 2, line 46, delete "para-aminobenze-" and substitute therefor --para-aminobenzenesulfonamide--.

Column 2, line 47, delete "nesulfanilamide".

UNITED STATES PATENT AND TRADEMARK OFFICE
CERTIFICATE OF CORRECTION

PATENT NO. : 5,510,387
DATED : APRIL 23, 1996
INVENTOR(S) : Nikolai B. LEONIDOV and Nikolai G. SELEZNEV It is certified that error appears in the above-indentified patent and that said Letters Patent is hereby corrected as shown below:

Column 2, line 49, delete "para-aminobenzenesulfanilamide" and substitute therefor --para-aminobenzenesulfonamide--.

Column 2, line 57, delete "para-aminobenzenesulfanilamide" and substitute therefor --para-aminobenzenesulfonamide--.

Column 3, line 1, delete "para-aminoben-" and substitute therefor --para-aminobenzenesulfonamide--.

Column 3, line 2, delete "zenesulfanilamide".

Column 3, line 10, delete "para-aminobenzene-" and substitute therefor --para-aminobenzenesulfonamide--.

Column 3, line 11, delete "sulfanilamide".

Column 3, line 55, delete "para-aminobenzenesulfanilamide" and substitute therefor --para-aminobenzenesulfonamide--.

UNITED STATES PATENT AND TRADEMARK OFFICE
CERTIFICATE OF CORRECTION

PATENT NO. : 5,510,387
DATED : APRIL 23, 1996
INVENTOR(S) : Nikolai B. LEONIDOV and Nikolai G. SELEZNEV It is certified that error appears in the above-indentified patent and that said Letters Patent is hereby corrected as shown below:

Column 3, line 56, delete "para-aminobenzenesulfanilamide" and substitute therefor --para-aminobenzenesulfonamide--.

Column 4, line 6 (i.e., Table 1, line 3), delete "Para-Aminobenzenesulfanilamide" and substitute therefor --Para-aminobenzenesulfonamide--.

Column 4, line 12 (i.e., Table 1, line 8), delete "para-".

Column 4, line 13 (i.e., Table 1, line 9), delete "aminobenzene-" and substitute therefor --para-aminobenzenesulfonamide--.

Column 4, line 14 (i.e., Table 1, line 10), delete "sulfanilamide".

Column 4, line 16 (i.e., Table 1, line 12), delete "para-aminobenzene-" and substitute therefor --para-aminobenzenesulfonamide--.

UNITED STATES PATENT AND TRADEMARK OFFICE
CERTIFICATE OF CORRECTION

PATENT NO. : 5,510,387
DATED : APRIL 23, 1996
INVENTOR(S) : Nikolai B. LEONIDOV and Nikolai G. SELEZNEV It is certified that error appears in the above-indentified patent and that said Letters Patent is hereby corrected as shown below:

Column 4, line 61 (i.e., Table 2, line 10), delete "aminoben-" and substitute therefor --para-aminobenzenesulfonamide--.

Column 4, line 62 (i.e., Table 2, line 11), delete "zenesulfanila-".

Column 4, line 63 (i.e., Table 2, line 12), delete "mide".

Column 5, line 58 (i.e., Table 3, line 11), delete "para-".

Column 5, line 59 (i.e., Table 3, line 12), delete "aminobenzenesulfanilamide" and substitute therefor --para-aminobenzenesulfonamide--.

Column 6, line 27 (i.e., Table 4, line 2), delete "sulfamilamide" and substitute therefor --sulfanilamide--.

Column 6, line 33 (i.e., Table 4, line 8), delete "para-".

UNITED STATES PATENT AND TRADEMARK OFFICE
CERTIFICATE OF CORRECTION

PATENT NO. : 5,510,387
DATED : APRIL 23, 1996
INVENTOR(S) : Nikolai B. LEONIDOV and Nikolai G. SELEZNEV It is certified that error appears in the above-indentified patent and that said Letters Patent is hereby corrected as shown below:

Column 4, line 17 (i.e., Table 1, line 13), delete "sulfanilamide".

Column 4, line 19 (i.e., Table 1, line 15), delete "para-".

Column 4, line 20 (i.e., Table 1, line 16), delete "aminobenzenesulfa-" and substitute therefor --para-aminobenzenesulfonamide--.

Column 4, line 21 (i.e., Table 1, line 17), delete "nilamide".

Column 4, line 24 (i.e., Table 1, line 20), delete "para-aminobenzene-" and substitute therefor --para-aminobenzenesulfonamide--.

Column 4, line 25 (i.e., Table 1, line 21), delete "sulfanilamide".

Column 4, line 60 (i.e., Table 2, line 9), delete "para-".

UNITED STATES PATENT AND TRADEMARK OFFICE
CERTIFICATE OF CORRECTION

PATENT NO. : 5,510,387
DATED : APRIL 23, 1996
INVENTOR(S) : Nikolai B. LEONIDOV and Nikolai G. SELEZNEV It is certified that error appears in the above-indentified patent and that said Letters Patent is hereby corrected as shown below:

Column 6, line 34 (i.e., Table 4, line 9), delete "aminobenzenesulfanilamide" and substitute therefor --para-aminobenzenesulfonamide--.

Column 6, line 42, between "are" and "evidence" delete "an".

Column 7, line 6, delete "para-".

Column 7, line 7, delete "aminobenzenesulfanilamide" and substitute therefor --para-aminobenzenesulfonamide--.

Column 7, line 35, delete "para-aminobenze-" and substitute therefor --para-aminobenzenesulfonamide--.

Column 7, line 36, delete "nesulfanilamide".

Column 8, line 42, delete "para-aminobenzenesulfanil-" and substitute therefor --para-aminobenzenesulfonamide,--.

Column 8, line 43, delete "amide,".

UNITED STATES PATENT AND TRADEMARK OFFICE
CERTIFICATE OF CORRECTION

PATENT NO. : 5,510,387
DATED : APRIL 23, 1996
INVENTOR(S) : Nikolai B. LEONIDOV and Nikolai G. SELEZNEV It is certified that error appears in the above-indentified patent and that said Letters Patent is hereby corrected as shown below:

Column 9, line 12, delete "para-aminobenzenesulfanil-" and substitute therefor --para-aminobenzenesulfonamide,--.

Column 9, line 13, delete "amide,".

Column 10, line 31, delete "para-aminobenzenesulfanilamide" and substitute therefor --para-aminobenzenesulfonamide--.

Column 10, line 44, delete "para-aminobenzenesulfanilamide" and substitute therefor --para-aminobenzenesulfonamide--.

Column 11, line 28, delete "para-".

Column 11, line 29, delete "aminobenzenesulfanilamide" and substitute therefor --para-aminobenzenesulfonamide--.

Column 12, line 1, delete "para-aminobenzenesulfanilamide" and substitute therefor --para-aminobenzenesulfonamide--.

Column 12, line 14 (i.e., Claim 1, line 3), delete "para-ami-".

UNITED STATES PATENT AND TRADEMARK OFFICE
CERTIFICATE OF CORRECTION

PATENT NO. : 5,510,387
DATED : APRIL 23, 1996
INVENTOR(S) : Nikolai B. LEONIDOV and Nikolai G. SELEZNEV It is certified that error appears in the above-indentified patent and that said Letters Patent is hereby corrected as shown below:

Column 12, line 15 (i.e., Claim 1, line 4), delete "nobenzenesulfanilamide" and substitute therefor --para-aminobenzenesulfonamide--.

Column 12, line 18 (i.e., Claim 2, line 2), delete "para-aminobenzenesulfanilamide" and substitute therefor --para-aminobenzenesulfonamide--.

Column 12, line 29 (i.e., Claim 5, line 2), delete "para-aminobenzenesulfanilamide" and substitute therefor --para-aminobenzenesulfonamide--.

Column 12, line 32 (i.e., Claim 6, line 2), delete "para-aminobenzenesulfanilamide" and substitute therefor --para-aminobenzenesulfonamide--.

Column 12, line 37 (i.e., Claim 7, line 3), delete "para-aminobenzene sul-" and substitute therefor --para-aminobenzenesulfonamide--.

UNITED STATES PATENT AND TRADEMARK OFFICE
CERTIFICATE OF CORRECTION

PATENT NO. : 5,510,387
DATED : APRIL 23, 1996
INVENTOR(S) : Nikolai B. LEONIDOV and Nikolai G. SELEZNEV It is certified that error appears in the above-indentified patent and that said Letters Patent is hereby corrected as shown below:

Column 12, line 38 (i.e., Claim 7, line 4), delete "fanilamide".

Signed and Sealed this

Twenty-sixth Day of November 1996

Attest:

BRUCE LEHMAN

Attesting Officer     Commissioner of Patents and Trademarks